United States Patent
Brookes (12)

(10) Patent No.: US 6,258,071 B1
(45) Date of Patent: Jul. 10, 2001

(54) MAGNETIC RESONANCE-COMPATIBLE NEEDLE

(76) Inventor: Jocelyn Asher Simon Brookes, Flat 6, Palm Court, No. 11 Fellows Road, London NW3 3LT (GB)

( * ) Notice: Subject to any disclaimer, the term of this patent is extended or adjusted under 35 U.S.C. 154(b) by 00 days.

(21) Appl. No.: 09/031,631

(22) PCT Filed: Aug. 30, 1996

(86) PCT No.: PCT/GB96/02086

§ 371 Date: Jul. 3, 2000

§ 102(e) Date: Jul. 3, 2000

(87) PCT Pub. No.: WO97/07746

PCT Pub. Date: Mar. 6, 1997

(30) Foreign Application Priority Data

Aug. 31, 1995 (GB) .................................................. 9517781

(51) Int. Cl.[7] .................................................. A61M 5/32
(52) U.S. Cl. .......................................... 604/272; 600/410
(58) Field of Search .................................. 604/264, 271, 604/272, 275; 600/407, 410, 411, 421, 423, 424, 425

(56) References Cited

U.S. PATENT DOCUMENTS

| | | | | |
|---|---|---|---|---|
| 5,654,059 | * | 8/1997 | Hecht .................................. | 428/65.9 |
| 5,699,801 | * | 12/1997 | Atalar et al. ....................... | 128/653.2 |
| 5,709,668 | * | 1/1998 | Wacks ................................. | 604/232 |
| 5,738,632 | * | 4/1998 | Karasawa ............................ | 600/410 |

OTHER PUBLICATIONS

PCT International Search for PCT/GB96/02086 with International Filing Date of Aug. 30, 1996.
PCT Written Opinion for PCT/GB96/02086, Date of Mailing Apr. 30, 1997.
Response to Written Opinion for PCT/GB96/02086, dated Jul. 21, 1997.
PCT Written Opinion for PCT/GM96/02086, Date of Mailing Aug. 21, 1997.
Tables of Physical and Chemical Constants, and Some Mathematical Functions, compiled by G.W.C. Kaye, O.B.E., M.A., D.Sc., F.R.S. and T. H. Lady, M.A., Sc.D., F.R.S., printed by William Clowes and Sons Ltd., London and Beccles, Thirteenth Edition Longmans, Green & Co., Ltd., 1966.
PCT Notification of Transmittal of the International Preliminary Examination Report for Pct/GB96/02086, Date of mailing Nov. 28, 1997.

* cited by examiner

*Primary Examiner*—Ronald K. Stright, Jr.
*Assistant Examiner*—Patricia Bianco
(74) *Attorney, Agent, or Firm*—Michael A. O'Neil

(57) ABSTRACT

A medical needle is made of non-metallic non-magnetic materials such that medical interventional procedures requiring needle access to people, animals or isolated tissues can be performed in a Magnetic Resonance Imaging (MRI) scanner without significant artefact or image distortion. The dimensions of the needle are adaptable to the task required.

6 Claims, 1 Drawing Sheet

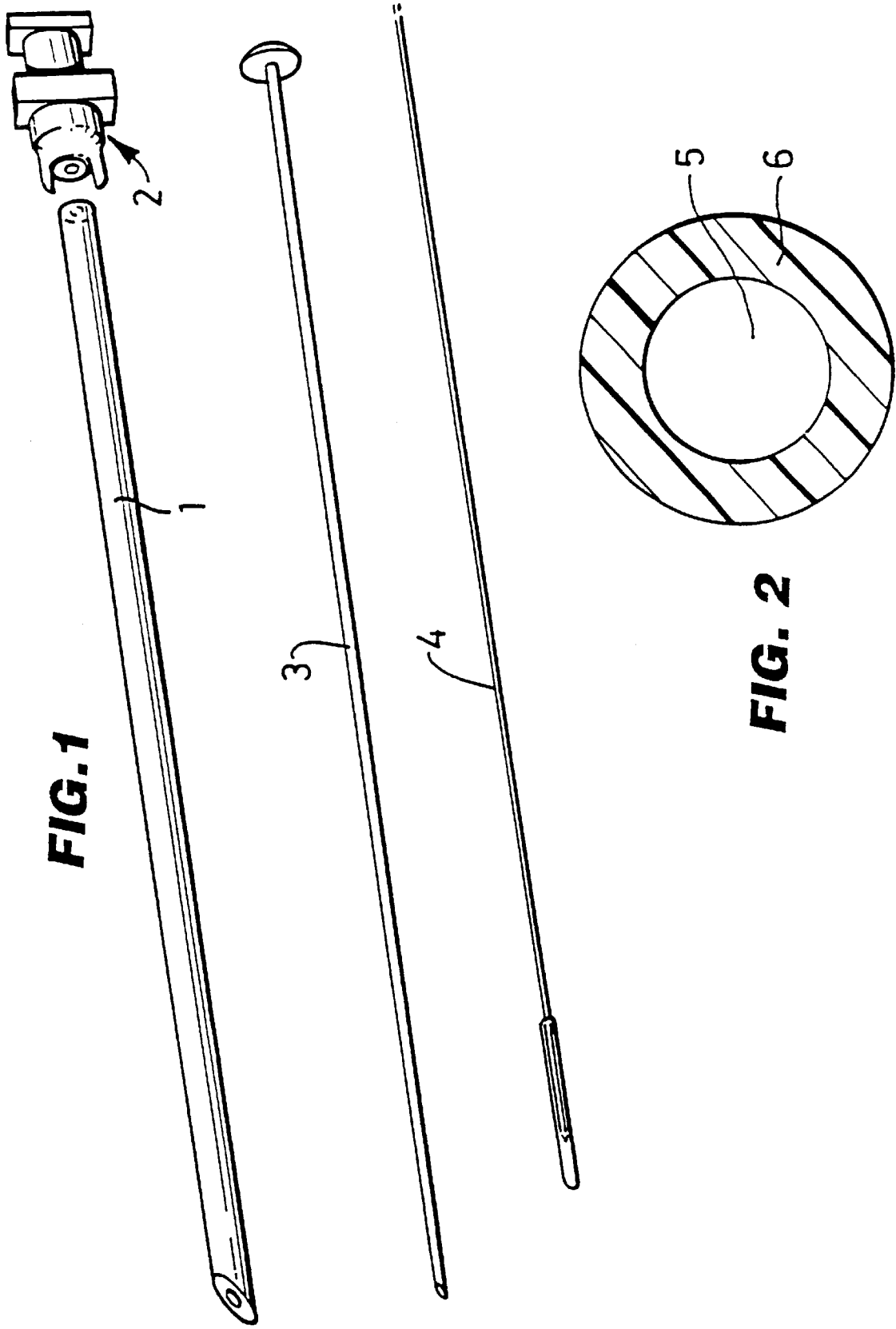

MAGNETIC RESONANCE-COMPATIBLE NEEDLE

TECHNICAL FIELD

This invention relates generally to needles of the type used in medical procedures and, more specifically, to needles in conjunction with MRI procedures.

BACKGROUND AND SUMMARY OF INVENTION

Magnetic Resonance Imaging (MRI) scanning is a method of imaging the human body or other fleshy objects, e.g., animals, either alive or dead. It depends on the object being placed in a large and uniform magnetic field (commonly ranging from 0.2–7.0 Tesla field strength according to the particular machine used).

The image is created by disturbance of molecules of the body by radio-frequency (RF) pulses causing resonance of these molecules. After the RF pulse, the molecules realign with the magnetic field and in so doing emit a weak RF signal of their own. This signal is detected and analyzed by a computer and a signal map created of the interrogated body part such that a grayscale image is displayed.

The appearance is usually that of "slices" through the body revealing the inner organs. It is useful in medical practice to place needles in these inner organs in the presence of disease both to extract tissue and fluid samples for analysis (biopsy) or to pass fluids or instruments down the needles to alter the tissue of interest in a variety of prespecified ways.

The precise position of the needle tip is clearly vital for accurate diagnosis and/or therapy in this context.

To use a needle in an MRI scanner, the needle must fulfill all the requirements for a medicinal needle in terms of strength and body compatibility as well as being compatible with MRI imaging apparatus in that it must be both clearly visible when scanned as well as causing no distortion artefact to the final stage. Any magnetic object will distort the magnetic field and thus the image, making accurate placement difficult.

Such needles as are used currently are made of metal alloys with high non-ferrous metal content and a low relative proportion of iron, but these still cause significant artefact, especially at the needle tip, the most important part.

According to the present invention, the needle is manufactured out of non-metallic materials such as carbon fiber, glass fiber, plastics or ceramics so as to cause no artefact on MRI scanning and allow non-distorted tip visualization.

In one embodiment of the invention, the needle is made of fiber composite materials such as carbon or glass fibers wherein the fibers are arranged either axially, spirally, in circular fashion, or in a combination of these orientations. In another embodiment of the invention, the needle is sterilizable by heat, chemicals, and/or irradiation techniques allowing re-use of the needle.

BRIEF DESCRIPTION OF THE DRAWINGS

A more complete understanding of the invention may be had by reference to the following Detailed Description when taken in conjunction with the accompanying Drawings, wherein:

FIG. 1 shows the side view of the needle and a selection of accompanying components.

FIG. 2 shows the needle end-on.

DETAILED DESCRIPTION

Referring now to the Drawings, and particularly to FIGS. 1 and 2, the needle comprises an outer cylindrical tube 1 of carbon fiber, glass fiber, plastic or ceramic material with length and dimensions of the wall 6 variable according to the task required, i.e., large or small needles.

The needle has a connector 2 attached to its proximal end to allow the connection of other apparatus.

The needle bore 5 allows passage of fluids in either direction, the insertion of an obturator, mandril, or trocar 3, as well as the passage of implements such as optical light fibers 4, catheters, and more complex instruments such as ultrasound probes.

The needle and trocar assembly can be adapted to perform core biopsies of tissues as is currently undertaken with metallic needles.

The carbon fiber tubing is manufactured either by "pultrusion" of the fibers over a mandril with the fibers arranged both axially and spirally, or wrapping preformed carbon fiber sheeting around a mandril with subsequent polishing of the surfaces.

It will of course be understood that the present invention has been described above purely by way of example, and that modification of detail can be made within the scope of the invention.

I claim:

1. A needle made of materials which are compatible for use in an MRI scanner wherein the material is wrapped carbon fiber and causes no significant artefact or image distortion when visualised with an MRI scanner.

2. A needle as claimed in claim 1 that is multipurpose, including as an aspiration biopsy needle.

3. A needle made of materials which are compatible for use in an MRI scanner wherein the material is axially pultruded carbon fiber and causes no significant artefact or image distortion when visualised with an MRI scanner.

4. A needle as claimed in claim 3 that is multipurpose, including as an aspiration biopsy needle.

5. A needle made of materials which are compatible for use in an MRI scanner wherein the material is spirally pultruded carbon fiber and causes no significant artefact or image distortion when visualised with an MRI scanner.

6. A needle as claimed in claim 5 that is multipurpose, including as an aspiration biopsy needle.

* * * * *